April 9, 1974 R. S. MOORE Plant Pat. 3,538
MINIATURE ROSE PLANT
Filed Sept. 14, 1972
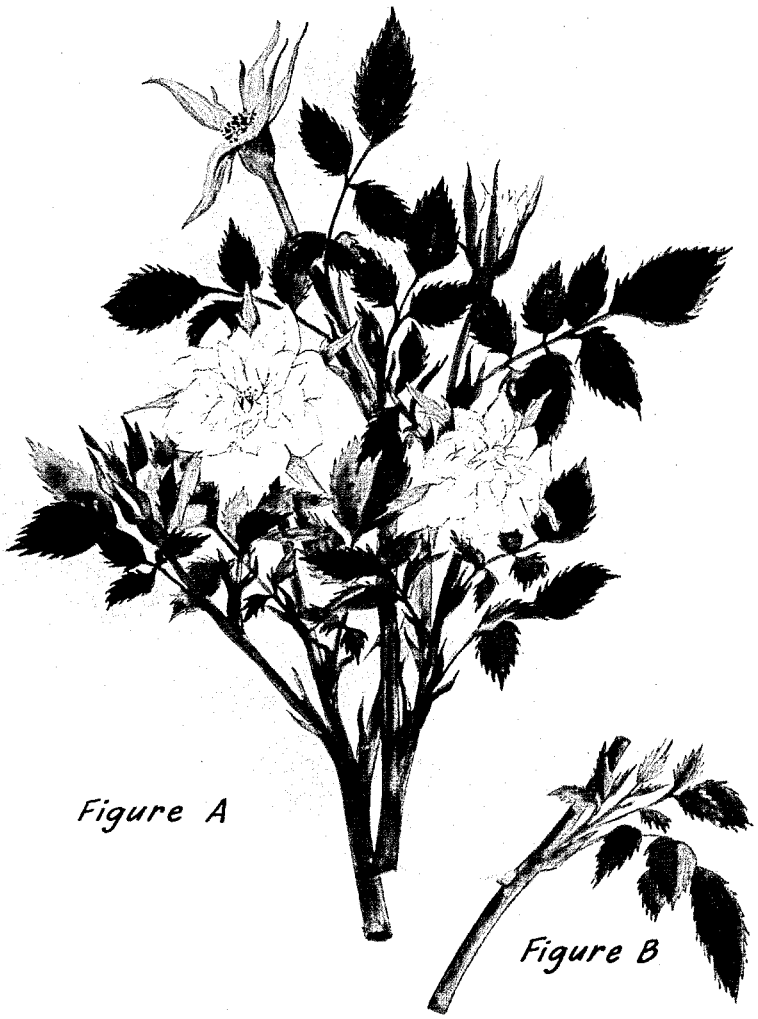
WITNESS
Jeanette Nunn Copley
INVENTOR
Ralph S. Moore United States Patent Office Plant Pat. 3,538
Patented Apr. 9, 1974

3,538

MINIATURE ROSE PLANT

Ralph S. Moore, 2519 E. Noble Ave.,
Visalia, Calif. 93277

Filed Sept. 14, 1972, Ser. No. 288,889
Int. Cl. A01h 5/00

U.S. Cl. Plt.—8 1 Claim

The present invention relates to a new and distinct variety of hardy, dwarf, bush type rose plant of the miniature class; the variety being primarily characterized—as to novelty—by buds and flowers of clear pure white blended with soft to very soft shades of yellow at base of buds and in center of opening flowers.

The variety is further characterized by:

An abundance of bloom, with flowers borne singly or several to the stem.

Light fragrance.

A plant which is vigorous, of rounded to spreading habit, and with semi-glossy, small to medium small foliage with pointed leaflets; the buds and flowers being similar in shape, but of smaller size, as compared to Jet Trail (U.S. Plant Pat. No. 2,683). The plant which has a normal height of 10" to 12" at maturity can easily be maintained at 10" or less with occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between an unnamed seedling (*Rosa wichuraiana* × Floradora—not patented) as the seed parent, and an unnamed seedling (Little Darling—U.S. Plant Pat. 1,581 × unnamed red miniature) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; garden decoration; potted plant.

Class: Miniature.

Flowers: Continuity—continuous; repeat blooms all season.

*Fragrance*—Slight to moderate.

Flowers borne: Singly and several together on medium length; sturdy, wire-like stem.

Quantity of bloom: Average abundance (or above) both outside and in greenhouse.

Bud:

*Peduncle.*—Medium length; erect; light green; essentially smooth surface.

*Before calyx breaks.*—Size, small.

*Form.*—Long pointed; with foliaceous appendages on surface of bud; with foliaceous parts extending beyond the tip of the bud equal to one half or more of its length.

*Color.*—Light to medium green.

*As calyx breaks.*—Color: white, lightly tinted greenish yellow.

*Form.*—Long pointed, becoming long urn-shaped as it opens.

*Opening.*—Usually opens well in all weather.

Bloom:

*Size when fully open.*—Small, averaging about 1" (2.5 centimeters).

*Petalage.*—Double—averaging about 30 petals arranged regularly.

*Form.*—Slightly rounded (high center) at first with petals rolled loosely outward, and later at maturity remaining loosely rolled outward with outer petals rolled more downward.

Petals: Rather thin; satiny both inside and outside.

*Shape.*—Outside petals broadly lanceolate with acute tip; inside petals—narrowly lanceolate, acute tip.

Color: Newly opened flower from a plant grown outdoors (September 1972) Visalia, Calif.

*Outside petal.*—Outside surface—nearly pure white shading into pale yellow thence to Canary yellow 2/2 (or lighter) at base; inside surface—nearly pure white shading into pale yellow thence to Canary yellow 2/2 at base.

*Intermediate petals.*—Similar to outside petal on both surfaces.

*Inside petal.*—Similar to intermediate petal on both surfaces but less white area and more soft yellow area—lighter yellow at base on both surfaces than intermediate petal.

*General color effect newly opened flower.*—White with very soft yellow in center of flower; outer petals often tipped pink in cooler weather. As flowers age petals become more white with tips often tinted pink, especially outdoors in cool weather.

*Behaviour.*—Spent blooms may persist for a time as flower ages, then petals usually drop clean.

*Flower longevity (April 1972).*—Bush in pot in greenhouse—5 to 8 days. Cut flowers at living room temperature—4 to 8 days.

Reproductive organs:

*Stamens.*—Average number; arranged irregularly about pistil.

*Filaments.*—Short; of varying length.

*Pollens.*—Very small amount; yellow.

*Pistils.*—Average.

*Styles.*—Medium length; bunched; pale yellow or near white color.

*Stigma.*—Pale, greenish white.

*Ovaries.*—All enclosed in calyx.

*Hips.*—None.

*Sepals.*—Permanent; spear shaped.

*Seeds.*—None.

Foliage:

*Leaves.*—Compound of five leaflets (occasionally 3); abundant; medium small; leathery; semi-glossy.

*Leaflets.*—Shape: fairly narrowly lanceolate; apex, acute; base, acute or nearly round. Margin, serrate. Color: normal light green. Rachis: medium strength; upper side, grooved; under side, few or no thorns. Stipules: medium to long; narrow width; short to medium length; points, turning out at an angle of about 45 degrees.

Growth:

*Habit.*—Dwarf; bushy; rounded to spreading (outdoors); much branched.

*Growth.*—Free; vigorous.

*Canes.*—Medium; slender.

*Main stems.*—Color: medium green—becomes grayish with age. Thorns: sparse. Prickles—none. Hairs—none.

*Branches.*—Color: medium green. Thorns: few or none; medium length; hooked slightly downward; medium to long oval base. Prickles—none. Hairs—none.

*New shoots.* Color: medium waxy green; sometimes tinted bronze. Thorns: few or none; medium length; hooked slightly downward; light brown to reddish; sharp points; base—short, oval. Pickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Jet Trail miniature rose (U.S. Plant Pat. No. 2,683) in general form of both bud and flower, but of somewhat smaller size, the color also being similar except that the present variety has more yellow in the bud and opening flower, the general color effect of the freshly opened flower being white to near white with the petal tips becoming pink as flower ages; and further characterized by a plant which is vigorous and compact in growth, easy to propagate from cuttings, with small semi-glossy foliage of a meduim green color and an abundance of bloom borne almost continuously throughout the growing season with flowers borne singly or several to the stem.

No references cited.

ROBERT E. BAGWILL, Primary Examiner